United States Patent [19]

Holler et al.

[11] 4,371,427

[45] Feb. 1, 1983

[54] EXTRACTIVE DISTILLATION

[75] Inventors: Raymond E. Holler; Loyal E. Henson, both of Bartlesville, Okla.

[73] Assignee: Phillips Petroleum Company, Bartlesville, Okla.

[21] Appl. No.: 273,559

[22] Filed: Jun. 16, 1981

[51] Int. Cl.³ .............................................. B01D 3/42
[52] U.S. Cl. .......................................... 203/3; 203/56; 203/58; 203/DIG. 18; 208/DIG. 1; 585/857

[58] Field of Search ......................... 196/132; 203/1-3, 203/53, 56, DIG. 18, 58, 63; 208/DIG. 1; 202/160; 585/800, 833, 837, 838, 857

[56] References Cited

U.S. PATENT DOCUMENTS 3,607,665  9/1971  Rogers ............................... 202/160
4,298,363  11/1981  Campbell et al. ....................... 62/21

Primary Examiner—Frank Sever

[57] ABSTRACT

A level-controlled water tank in an extractive distillation system is used to maintain the water concentration in the solvent mixture constant.

14 Claims, 2 Drawing Figures 4,371,427

EXTRACTIVE DISTILLATION

BACKGROUND OF THE INVENTION

Mixtures of organic fluids can be separated efficiently in an extractive distillation process. In such a process a selective solvent is utilized. This selective solvent is believed to change the solubility behavior of the two ingredients to be separated. Extractive distillation processes have been considerably improved in recent years. One such improved extractive distillation process is described in U.S. Pat. No. 4,053,369. Whereas it was believed for some time that in an extractive distillation process one should avoid the formation of two or more liquid phases it was discovered that the establishment of two liquid phases in certain situations aids the efficiency of an extractive distillation process. Therefore, it is described in the patent cited that the provision of two immiscible liquid phases in the upper portion of an extractive distillation column advantageously influences the separation efficiency of such an extraction distillation column and process.

The normal extractive distillation utilizes an extractive distillation column and a stripper. These two units may be combined into one but essentially maintain their function. The stripper serves to recover the solvent from the extract whereas the raffinate is recovered from the overhead effluent of the extractive distillation column.

THE INVENTION

In extractive distillation operations utilizing a selective solvent and water in order to maximize the separation efficiency, the water balance in the system may constitute a problem. Specifically, the separation efficiency, is critically dependent in many instances upon a specific quantity of water in the extraction agent composed of the organic solvent and water. An accurate control of the water content in the extractive distillation column, a fast response in such a control system as well as the flexibility allowing adjustments in the water content when desired constitute the combined goal of the present invention.

It is thus one object of this invention to provide an extractive distillation system, process and apparatus, in which the water content can be accurately and quickly controlled. A further object of this invention is to provide such a system wherein the water content can be changed rapidly with or without adding make up water.

These and other objects, advantages, details, features and embodiments of this invention will become apparent to those skilled in the art from the following detailed description, the appended claims and the drawing which shows a schematic flow diagram of an extractive distillation system.

In accordance with this invention the extractive distillation system is provided wherein the overhead condensed water from the stripper is passed to a level controlled water tank and wherein the level controller manipulates directly or indirectly the flow of water from the water tank back into the extractive distillation column via the solvent feed tank. The flow of water from the water tank into the stripper is maintained at a desired rate independently of the level controller.

More specifically in accordance with a first embodiment of this invention an extractive distillation process is provided for which comprises the following steps. A hydrocarbon feed comprising a first and a second component is introduced into an extractive distillation column to be separated. These components can represent general classes of compounds, for example aromatic and non-aromatic hydrocarbons. This feed is extractively distilled in the extractive distillation column together with an extractive agent comprising a selective solvent and water. From the overhead of the distillation column the first component as well as a stream of liquid water is recovered. The bottom stream from the extractive distillation column is introduced into a stripper. Steam is introduced into the lower portion of this stripper and an overhead stream is withdrawn from the stripper as well as a bottoms stream. The overhead stream from the stripper is condensed and a liquid water stream is withdrawn. The selective solvent from the stripper is reintroduced into the extractive distillation column via the solvent feed tank, and water from the condensed overhead stream from the stripper is evaporated to provide the steam for the stripper. In accordance with this invention the liquid water from the stripper overhead stream is introduced into a water tank which has a level controller associated therewith. Optionally and preferably also at least a portion of the liquid water stream from the extractive distillation column removed overhead is introduced into this water tank. A stream of stripper water is withdrawn from the water tank in a flow controlled manner whereas a distillation water stream is withdrawn from this water tank responsive to a level controller signal generated by the level controller associated with the water tank. This distillation water stream, as well as the selective solvent stream and any remainder of the liquid water withdrawn overhead from the extractive distillation column that has not been introduced into the water tank as well as the distillation water stream are combined to form the stream of the agent used in the extractive distillation step.

In accordance with a second embodiment of this invention an apparatus for carrying out the process is provided for. This apparatus comprises as its main components an extractive distillation column, a first condenser, a stripper, a second condenser, a water tank, a stripper water conduit, a flow controller, extractive agent conduit means and means for connecting the water outlet of the overhead of the extractive distillation column at least indirectly with the inlet of the agent into the extractive distillation column. The extractive distillation column is connected with the first condenser in the usual way to allow the withdrawal of the raffinate, reflux and the withdrawal of condensed water. The bottom of the extractive distillation column is connected with the stripper and the second condenser is connected with the stripper overhead in the usual way to allow the withdrawal of an overhead extract stream and a condensed water stream. In accordance with this invention a water tank is provided for which has associated therewith a water level control signal generator. The water from this water tank is removed via two conduits. The first conduit furnishes the water to a steam generator for the stripper. The flow of water in this first conduit is controlled independently of the level in the water tank and thus independently of the water level control signal generated by the respective generator. The flow into the steam generator can be simply flow controlled. The flow of the water through a second conduit is controlled responsive to the water level controlled signal either directly or indirectly. The flow of water in this second conduit is introduced into the extractive distillation column via the solvent tank as part of said extractive agent. In a presently preferred embodiment the water outlet of the overhead condenser associated with the extractive distillation column is connected with the water tank so that any water leaving the extractive distillation column overhead is introduced into the water tank and a corresponding quantity from there is reintroduced into the extractive distillation column via the solvent tank.

The water tank provided for in accordance with this invention with the level controller has several significant advantages. First, the water tank allows readily an addition of water to the system by, for instance, water make-up means connected via a valve to the water tank. Second and in some instances more importantly, the water content in the agent can be adjusted very rapidly and accurately by simply changing the level in the water tank, e.g., by changing a water level set point of the water level controller. By lowering the water level set point in the water tank the corresponding quantity of water is introduced into the extractive distillation system thereby raising the water level in the agent correspondingly. Vice versa by raising the water level in the water tank the quantity of water in the extractive distillation column is reduced correspondingly. Therefore a simple calibration of the water tank level set point allows the precise adjustment of the water percentage in the extractive distillation column quickly and accurately.

The present invention is particularly desirable and applicable in situations where one or more of the following conditions and process parameters occur. These conditions and process parameters are intended to describe preferred embodiments of this invention but are intended not to unduly limit the scope thereof.

The following tabulation shows typical feedstock mixtures, solvents and water contents for an efficient extractive distillation operation.

TABLE

| Feedstock | Selective Solvent | Wt. % Water |
|---|---|---|
| Paraffin/aromatic | Sulfolanes | 3.75 |

Generally speaking this process will be advantageously used in situations where the water content in the combined agent (selective solvent and water) is in the range of 1 to 10 weight percent.

Figure 1:
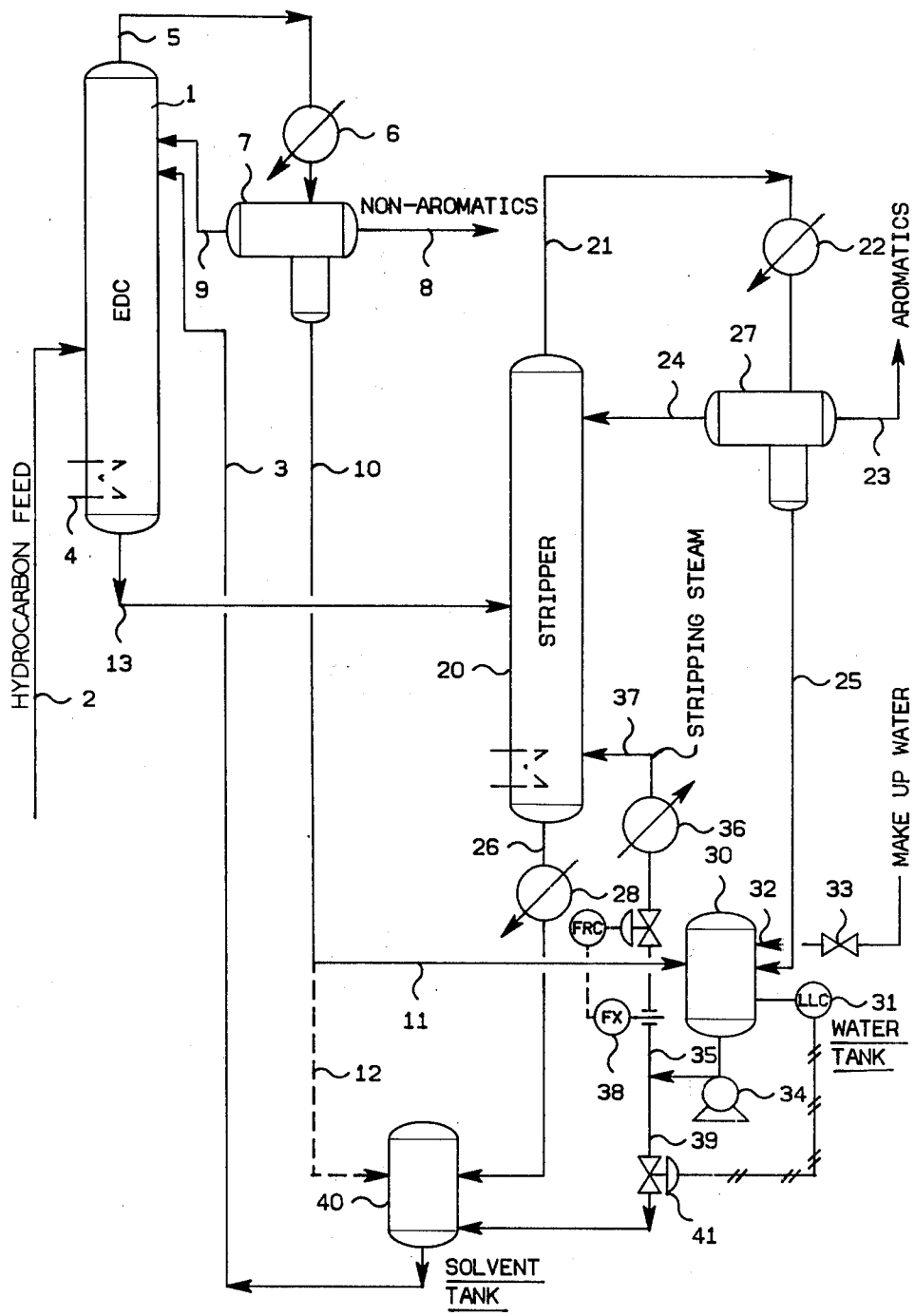
FIG. 1 depicts both embodiments of the invention.

Typically the total quantity of water present in the stripper, the overhead condenser associated therewith and the water tank will be about 4 to 40 times the total quantity of water present in the extractive distillation column, the overhead condenser associated therewith and (if used) an agent tank. The drawing shows a schematic flow diagram of an extractive distillation system utilizing the present invention. Into an extractive distillation column 1 a hydrocarbon feedstock is introduced via line 2. The extraction agent is introduced into the extractive distillation column 1 via line 3. The extraction agent comprises the selective solvent and water. The extractive distillation is heated by means of a heater 4. The gaseous overhead effluent from the extractive distillation column is withdrawn via line 5, condensed in condenser 6, and phase separated in the vessel 7. From vessel 7 the nonaromatics, e.g., the paraffins are withdrawn via line 8. A portion of the organic material in drum 7 is reintroduced into the extractive distillation column via line 9 as reflux. The water phase is withdrawn from vessel 7, more specifically from the settling leg thereof, via line 10. The water in line 10 is preferably introduced into the water tank 30 via line 11 but can also be completely or partially introduced in the solvent tank 40 via line 12 which is shown as a dotted line in the drawing. Another possibility would be to introduce the water from line 10 into the overhead collecting vessel 27 associated with the stripper 20.

The bottom effluent from the extractive distillation column 1 is withdrawn via line 13. This effluent comprises mainly the aromatic extract and the selective solvent. This stream from line 13 is introduced into the stripper 20. In the stripper 20 the bottom effluent is contacted with steam, and a mixture of aromatics and steam are withdrawn from the stripper 20 overhead via line 21. This stream is condensed in cooler 22 and allowed to settle in settler 27. An aromatic product stream is withdrawn from settler 27 via line 23 and a part of the aromatic stream is reintroduced into the stripper via line 24 as a reflux. The condensed steam is separated from the settler 27, more specifically from the settling leg thereof via line 25, and this water is introduced into the water tank 30. The bottom stream of the stripper 20 is passed via line 26 and a cooler 28 to the solvent tank 40.

The water tank 30 is provided with a level controller 31. Furthermore a water make-up line 32 associated with a valve 33 is provided for. The water from water tank 30 is withdrawn by means of a pump 34. The largest quantity of the water is passed via line 35 through a steam generator 36. The flow of water into the steam generator and from there via line 37 into the stripper is controlled by a flow control unit 38. This flow controller is a standard flow controller and needs no further description.

The minor portion of the water withdrawn from the water tank 30 by means of pump 34 is passed via line 39 through a valve 41 to the solvent tank 40. This valve 41 is controlled by the level controller 31.

Solvent and water together as the extracting agent are withdrawn from tank 40 and passed via line 3 back into the extractive distillation column 1.

Most preferably the liquid level controller 31 is provided with a set point that is adjustable. By adjusting the set point the quantity of water in solvent tank 40, extractive distillation column 1, and separation vessel 7 can be adjusted up or down.

For adequate speed of response it is desirable to use a cross section A(in$^2$) of tank 30 that is related to the quantity of water W(gal.) circulating in the stripper. This relationship can be expressed as follows:

$$A = k \cdot W$$

wherein k is set at a value in the range of about 5 to 200.

In the following, specific examples are given which are intended to illustrate but not unduly limit the present invention.

EXAMPLE

A pilot plant extractive distillation was carried out essentially as described in connection with FIG. 1 using sulfolane with water as the solvent. A full-range benzene-toluene-xylene (C$_6$ to C$_9$) reformate was used as the feedstock. The operating conditions, quantities used, etc. as well as the results obtained are shown in the following table. The main difference between the individual runs resides in the water content of the lean solvent.

EXAMPLE

A pilot plant extractive distillation was carried out essentially as described in connection with FIG. 1 using sulfolane with water as the solvent. A full-range benzene-toluene-xylene ($C_6$ to $C_9$) reformate was used as the feedstock. The operating conditions, quantities used etc. as well as the results obtained are shown in the following Table. The main difference between the individual runs resides in the water content of the lean solvent.

TABLE 1
OPERATING DATA FROM EXTRACTIVE DISTILLATION PILOT PLANT
SYSTEM: SULFOLANE & WATER - ($C_6$ to $C_9$) EFFLUENT

| RATES, LB/HR. | RUN NO. | | | | | | | | | |
|---|---|---|---|---|---|---|---|---|---|---|
| | 7 | 5 | 1 | 2 | 3 | 4 | 6 | 8 | 9 | 10 |
| Solvent | 210 | 210 | 210 | 210 | 210 | 210 | 210 | 210 | 210 | 210 |
| H.C. FEED(1) | 70 | 70 | 70 | 70 | 70 | 70 | 70 | 70 | 70 | 70 |
| EDC OHP(2) | 37.2 | 34.1 | 32.4 | 34.6 | 34.9 | 36.0 | 37.0 | 38.9 | 40.2 | 39.6 |
| STR. OHP(3) | 32.8 | 35.9 | 37.7 | 35.4 | 35.1 | 34.0 | 33.0 | 31.1 | 29.9 | 30.4 |
| EDC REFLUX | 13.0 | 13.0 | 13.0 | 13.0 | 13.0 | 13.0 | 13.0 | 13.0 | 13.0 | 13.0 |
| STRIPPING $H_2O$ | 20.0 | 20.0 | 20.0 | 20.0 | 20.0 | 20.0 | 20.0 | 20.0 | 20.0 | 20.0 |
| EDC CONDITIONS | | | | | | | | | | |
| KETTLE, °F. | 306 | 306 | 309 | 313 | 314 | 306 | 311 | 308 | 305 | 308 |
| TRAY 13, °F. | 215 | 216 | 216 | 218 | 219 | 216 | 216 | 215 | 213 | 214 |
| TRAY 25, °F. | 208 | 208 | 207 | 206 | 208 | 206 | 209 | 208 | 207 | 209 |
| TRAY 37, °F. | 203 | 203 | 204 | 205 | 205 | 203 | 203 | 203 | 203 | 203 |
| TRAY 40, °F. | 216 | 218 | 223 | 221 | 221 | 219 | 218 | 217 | 215 | 215 |
| TRAY 62, °F. | 225 | 220 | 223 | 223 | 223 | 221 | 220 | 219 | 216 | 217 |
| TRAY 74, °F. | 189 | 193 | 202 | 200 | 197 | 195 | 190 | 194 | 192 | 186 |
| REFLUX, °F. | 215 | 215 | 217 | 219 | 222 | 220 | 221 | 222 | 220 | 210 |
| SOLVENT, °F. | 179 | 178 | 185 | 184 | 185 | 185 | 186 | 184 | 185 | 178 |
| HC FEED, °F. | 216 | 218 | 221 | 222 | 220 | 221 | 219 | 217 | 215 | 217 |
| PRESS. PSIG | 4.0 | 4.0 | 3.0 | 3.0 | 3.0 | 3.0 | 3.0 | 3.0 | 3.5 | 4.0 |
| SOL./FEED(4) | 3.0 | 3.0 | 3.0 | 3.0 | 3.0 | 3.0 | 3.0 | 3.0 | 3.0 | 3.0 |
| SOL./REFLUX | 16.2 | 16.2 | 16.2 | 16.2 | 16.2 | 16.2 | 16.2 | 16.2 | 16.2 | 16.2 |
| FEED TRAY LOC. 37 | 37 | 37 | 37 | 37 | 37 | 37 | 37 | 37 | 37 | 37 |
| SPLIT (B/F), %(5) | 0.47 | 0.51 | 0.54 | 0.51 | 0.50 | 0.49 | 0.47 | 0.44 | 0.43 | 0.43 |
| ΔP, SEC. A, "$H_2O$(6) | 60 | 56 | 46 | 50 | 52 | 55 | 60 | 60 | 66 | 69 |
| ΔP, SEC. B, "$H_2O$ | 41 | 43 | 31 | 34 | 35 | 36 | 39 | 40 | 43 | 45 |
| STR. CONDITIONS | | | | | | | | | | |
| KETTLE, °F. | 317 | 319 | 320 | 319 | 319 | 318 | 318 | 319 | 316 | 319 |
| PRESS., "Hg. VAC. | 18.0 | 19.0 | 18.0 | 18.0 | 18.0 | 18.0 | 18.0 | 18.0 | 18.0 | 19.0 |
| ANALYSIS (WT. %) | | | | | | | | | | |
| FEED: | | | | | | | | | | |
| NON-AROMATICS | 42.11 | 40.07 | 42.62 | 42.96 | 43.07 | 43.50 | 43.22 | 43.76 | 44.82 | 42.46 |
| BENZENE | 3.51 | 3.31 | 3.32 | 3.42 | 3.52 | 3.57 | 3.46 | 3.56 | 3.68 | 3.63 |
| TOLUENE | 15.73 | 15.17 | 15.21 | 14.87 | 14.86 | 14.88 | 14.66 | 14.84 | 15.26 | 15.80 |
| $C_8$ AROMATICS | 29.72 | 31.87 | 30.02 | 29.94 | 29.47 | 29.35 | 29.60 | 29.05 | 28.64 | 29.40 |
| $C_9$+ AROMATICS | 8.93 | 9.58 | 8.83 | 8.82 | 9.08 | 8.70 | 9.05 | 8.80 | 7.59 | 8.71 |
| EDC OHP: | | | | | | | | | | |
| NON-AROMATICS | 79.27 | 82.35 | 90.75 | 86.81 | 86.43 | 84.63 | 81.83 | 78.73 | 78.15 | 75.08 |
| BENZENE | 6.87 | 6.95 | 6.50 | 6.90 | 6.99 | 7.14 | 6.88 | 6.57 | 6.46 | 6.69 |
| TOLUENE | 11.98 | 9.35 | 2.40 | 5.09 | 5.79 | 7.18 | 9.69 | 11.60 | 13.50 | 15.68 |
| $C_8$ AROMATICS | 1.45 | 1.02 | 0.28 | 0.84 | 0.60 | 0.72 | 1.90 | 2.32 | 1.49 | 2.03 |
| $C_9$+ AROMATICS | 0.43 | 0.33 | 0.08 | 0.36 | 0.19 | 0.33 | 0.51 | 0.77 | 0.39 | 0.52 |
| STR. OHP: | | | | | | | | | | |
| NON-AROMATICS | 0.00 | 0.00 | 1.27 | 0.15 | 0.03 | 0.00 | 0.00 | 0.00 | 0.00 | 0.00 |
| BENZENE | 0.02 | 0.04 | 0.53 | 0.17 | 0.11 | 0.05 | 0.03 | 0.00 | 0.00 | 0.00 |
| TOLUENE | 19.36 | 20.84 | 25.34 | 24.14 | 23.15 | 22.09 | 19.96 | 18.16 | 16.52 | 15.22 |
| $C_8$ AROMATICS | 61.96 | 60.65 | 56.46 | 58.13 | 58.55 | 59.91 | 61.34 | 62.66 | 65.22 | 64.69 |
| $C_9$+ AROMATICS | 18.67 | 18.47 | 16.41 | 17.41 | 18.18 | 17.95 | 18.68 | 19.19 | 18.26 | 20.09 |
| $H_2O$ IN LEAN SOLVENT, WT. % | 4.8 | 4.1 | 2.4 | 3.2 | 3.4 | 4.0 | 4.6 | 5.5 | 6.1 | 5.8 |
| AROMATIC RECOVERY, % | 80.98 | 85.67 | 92.55 | 88.58 | 88.13 | 86.02 | 83.10 | 78.98 | 77.29 | 75.51 |
| TX(7) RECOVERY, % | 84.39 | 89.32 | 97.27 | 93.50 | 92.85 | 90.90 | 87.22 | 82.47 | 80.64 | 78.14 |

TABLE 1-continued

OPERATING DATA FROM EXTRACTIVE DISTILLATION PILOT PLANT
SYSTEM: SULFOLANE & WATER - (C₆ to C₉) EFFLUENT

| RATES, LB/HR. | RUN NO. | | | | | | | | |
|---|---|---|---|---|---|---|---|---|---|
| | 7 | 5 | 1 | 2 | 3 | 4 | 6 | 8 | 9 | 10 |
| AROMATIC PURITY, % | 100.00 | 100.00 | 98.73 | 99.85 | 99.97 | 100.00 | 100.00 | 100.00 | 100.00 | 100.00 |

Figure 2:
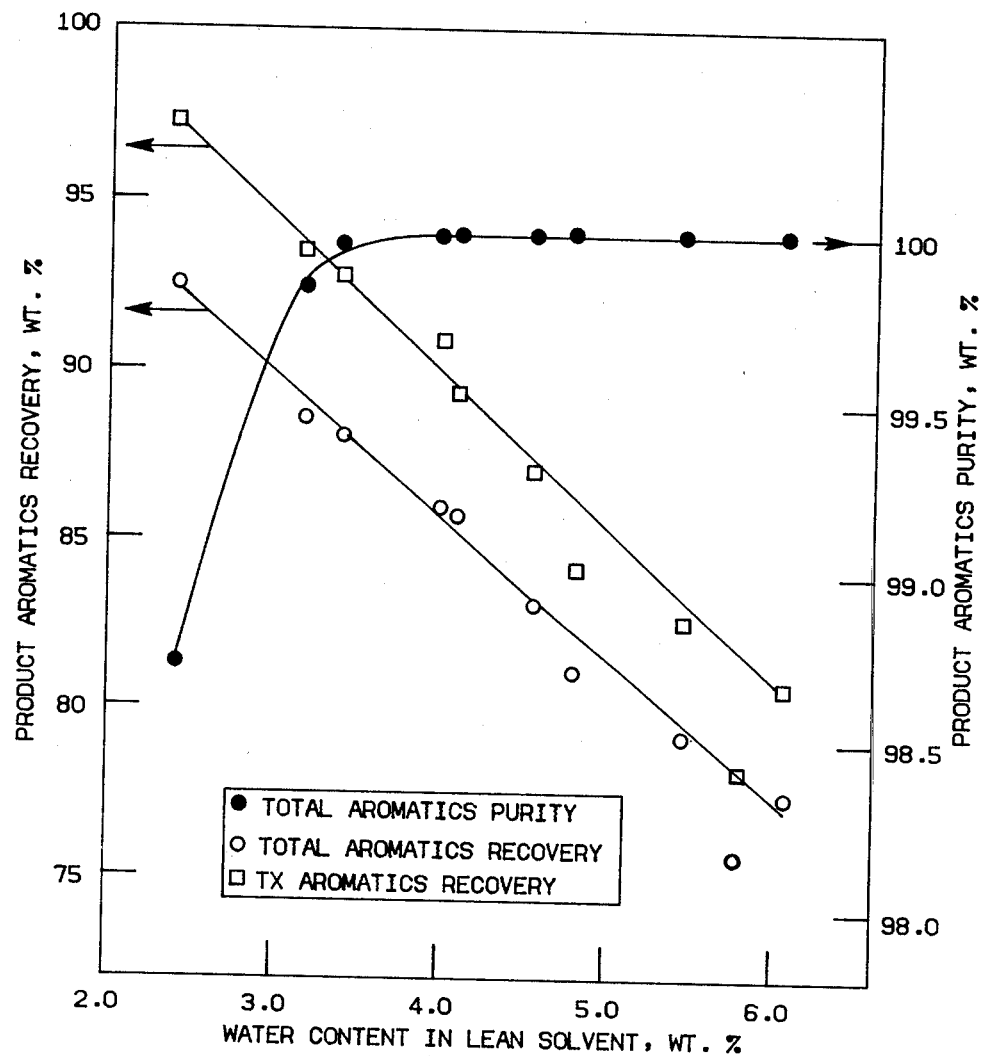
FIG. 2 depicts the effect of solvent water concentration on product purity.

(1)HC: Hydrocarbon
(2)EDC: Extractive distillation column, OHP: overhead product
(3)STR: Stripper
(4)SOL: Solvent
(5)SIF: Bottoms to feed (weight percentage)
(6)Pressure difference in upper (lower) section A(B) of column
(7)Toluene-xylene The data presented in FIG. 2 and Table 1 show the strong effect of solvent water content for purifying a full-range benzene-toluene-xylene reformate. An optimum solvent water content for this feed would be about 3.0 wt. %, where 99.5+% purity aromatics are obtained at 90.0% recovery. If the water content varied from ±0.4 wt. % of this set point the purity would vary from 99.2 to 99.96 wt. % and the aromatics recovery would vary from 91.5 to 88%. These variations would be unacceptable if a 99.5% purity product specification was to be made. Also, by properly controlling the solvent water, the column operates substantially better, with much less erratic behavior.

We claim:

1. In an extractive distillation process comprising
   (a) introducing a hydrocarbon feed comprising a first component and a second component to be separated in an extractive distillation column,
   (b) extractively distilling said hydrocarbon together with a stream of an extractive agent comprising a selective solvent and a required effective concentration of water in said extractive distillation column such as to form a first overhead stream and a first bottom stream,
   (c) recovering said first component and a first stream of liquid water from said first overhead stream,
   (d) introducing said first bottom stream into a stripper,
   (e) introducing steam into the lower portion of said stripper,
   (f) withdrawing a second overhead stream from said stripper,
   (g) withdrawing a second bottom stream from said stripper,
   (h) separating a second stream of liquid water from said second overhead stream,
   (i) evaporating water from said second stream of liquid water and using the so evaporated water as said steam,
   (j) withdrawing a selected solvent stream from said stripper, the improvement comprising
   (k) introducing said second stream of liquid water into a water tank having a level controller associated therewith which is capable of generating a level control signal responsive to the level of water in said tank,
   (l) withdrawing a flow controlled stripper water stream and a distillation water stream from said water tank under conditions so that said effective concentration of water in said distillation water stream is controlled responsive to said level control signal,
   (m) combining said selective solvent stream, said first stream of liquid water and said distillation water stream to form said stream of said extractive agent.

2. A process in accordance with claim 1 wherein all of said first stream of liquid water is introduced into said water tank.

3. A process in accordance with claim 1 wherein
   (a) said first overhead stream is condensed and separated into a first reflux stream, a first product stream comprising said first component and into said first water stream,
   (b) said second overhead stream is condensed and separated into a second reflux stream, a second product stream comprising said second component and into said second water stream,
   (c) said first reflux stream is introduced into the upper section of said extractive distillation column,
   (d) said second reflux stream is introduced into the upper section of said stripper, and
   (e) said second bottom stream from said stripper is said selective solvent stream.

4. A process in accordance with claim 1 wherein said level control signal directly controls the flow of liquid water in said distillation water stream.

5. A process in accordance with claim 4 wherein said level control signal controls a valve in a conduit through which only said distillation water stream flows.

6. A process in accordance with claim 1 comprising determining the water content in said extractive agent and responsive thereto adjusting the level controller in said water tank so that the quantity of water in said extractive agent reaches the desired value.

7. Apparatus for carrying out a process of claim 1 comprising
   (a) an extractive distillation column having
      a first feed inlet,
      a first overhead outlet,
      a first bottom outlet,
      an extractive agent inlet, and
      a first reflux inlet,
   (b) a first condenser and phase separator having
      a first condenser inlet connected to said first overhead outlet,
      a first product outlet,
      a first water outlet, and
      a first reflux outlet connected to said first reflux inlet,
   (c) a stripper having
      a second feed inlet connected to said first bottom outlet
      a second overhead outlet,
      a second bottom outlet,
      a second reflux inlet, and
      a stream inlet connected to a steam generator, (d) a second condenser and phase separator having
   a second condenser inlet connected to said second overhead outlet,
   a second product outlet,
   a second water outlet, and
   a second reflux outlet connected to said second reflux inlet,
(e) a water tank having
   water tank inlet means,
   water tank outlet means, and
   a water level control signal generator,
(f) a stripper water conduit connecting said water outlet means and said stream generator for converting water from said water tank to steam and introducing said steam into the stripper,
(g) a flow controller associated with said stripper water conduit controlling the flow of water through said steam generator and into said stripper,
(h) a conduit means connecting said extractive agent inlet with said second bottom outlet and also operatively connecting said extractive agent inlet with said water tank outlet means so that said signal generator causes flow of all of the water from said water tank that does not flow into the stripper to flow to said extractive agent inlet, and
(i) means for connecting said first water outlet directly or indirectly; with said extractive agent inlet so that the quantity of water leaving via said first water outlet is reintroduced into said extractive distillation column.

8. Apparatus in accordance with claim 7 wherein said conduit means comprises a extractive agent tank connected
   (a) with said second bottom outlet of said stripper to receive the bottom stream from said stripper,
   (b) with said water tank outlet means to receive water from said water tank in a quantity responsive to the signal of said level control signal generator, and
   (c) with said extractive agent inlet to supply said extractive agent to said extractive distillation column.

9. Apparatus in accordance with claim 7 wherein a flow control valve in a conduit connecting said extractive agent tank and said water tank is operatively connected with said level control signal generator.

10. Apparatus in accordance with claim 7 comprising a water make up means operatively connected to said water tank.

11. Process in accordance with claim 1 wherein said level controller is adjusted responsive to a determination of the water content in said extractive agent in order to change the total content of water flowing through the extractive distillation column.

12. Process in accordance with claim 1 wherein the set point of the water level in said water tank responsive to which said water level in the water tank is controlled is manipulated responsive to the determination of the concentration of water in the extractive agent flowing in the extractive distillation column.

13. In an extractive distillation process comprising
   (a) introducing a hydrocarbon feed comprising a first component and a second component to be separated into an extractive distillation column,
   (b) extractively distilling said hydrocarbon together with a stream of an extractive agent comprising a selective solvent and a required effective concentration of water in said extractive distillation column such as to form a first overhead stream and a first bottom stream,
   (c) recovering said first component and a first stream of liquid water from said first overhead stream,
   (d) introducing said first bottom stream into a stripper,
   (e) introducing steam into the lower portion of said stripper,
   (f) withdrawing a second overhead stream from said stripper,
   (g) withdrawing a second bottom stream from said stripper,
   (h) separating a second stream of liquid water from said second overhead stream,
   (i) evaporating water from said second stream of liquid water and using the so evaporated water as said steam,
   (j) withdrawing a selected solvent stream from said stripper, the improvement comprising
   (k) introducing said second stream of liquid water and at least a portion of said first stream of liquid water into a water tank having a level controller associated therewith which is capable of generating a level control signal responsive to the level of water in said tank,
   (l) withdrawing a flow controlled stripper water stream and a distillation water stream from said water tank under conditions so that said effective concentration of water in said distillation water stream is controlled responsive to said level control signal,
   (m) combining said selective solvent stream, any remainder of said first stream of liquid water and said distillation water stream to form said stream of said extractive agent.

14. In an extractive distillation process comprising an extractive distillation in the presence of a solvent and a required effective concentration of water in an extractive distillation column and stripping solvent in a stripper in the presence of steam and comprising a first water loop through the extractive distillation column and a second water loop through the stripper,
   the improvement comprising
   incorporating a water tank into the second water loop,
   controlling the flow of water from said second water loop to said first water loop responsive to the water level in said water tank sufficient to maintain required effective concentration.

* * * * *